United States Patent [19]
Hochshuler et al.

[11] Patent Number: 6,080,193
[45] Date of Patent: Jun. 27, 2000

[54] ADJUSTABLE HEIGHT FUSION DEVICE

[75] Inventors: Stephen H. Hochshuler, Dallas; Erik J. Wagner, Allen; Ralph F. Rashbaum; Richard D. Guyer, both of Dallas, all of Tex.

[73] Assignee: Spinal Concepts, Inc., Austin, Tex.

[21] Appl. No.: 09/153,178

[22] Filed: Sep. 15, 1998

Related U.S. Application Data

[62] Division of application No. 08/847,172, May 1, 1997.

[51] Int. Cl.⁷ ........................................... A61F 2/44
[52] U.S. Cl. ................................................. 623/17
[58] Field of Search .................. 623/16, 17, 18; 606/61

[56] References Cited

U.S. PATENT DOCUMENTS

| | | |
|---|---|---|
| 4,401,112 | 8/1983 | Rezaian . |
| 4,433,677 | 2/1984 | Ulrich et al. . |
| 4,492,226 | 1/1985 | Belykh et al. . |
| 4,501,269 | 2/1985 | Bagby . |
| 4,503,848 | 3/1985 | Caspar et al. . |
| 4,570,618 | 2/1986 | Wu . |
| 4,604,995 | 8/1986 | Spephens et al. . |
| 4,641,636 | 2/1987 | Cotrel . |
| 4,643,178 | 2/1987 | Nastari et al. . |
| 4,743,256 | 5/1988 | Brantigan . |
| 4,763,644 | 8/1988 | Webb . |
| 4,805,602 | 2/1989 | Puno et al. . |
| 4,834,757 | 5/1989 | Brantigan . |
| 4,878,915 | 11/1989 | Brantigan . |
| 4,887,596 | 12/1989 | Sherman . |
| 4,946,458 | 8/1990 | Herma et al. . |
| 4,950,269 | 8/1990 | Gaines, Jr. . |
| 4,961,740 | 10/1990 | Ray et al. . |
| 4,966,600 | 10/1990 | Songer et al. . |
| 4,987,892 | 1/1991 | Krag et al. . |
| 5,005,562 | 4/1991 | Cotrel . |

(List continued on next page.)

FOREIGN PATENT DOCUMENTS

| | | |
|---|---|---|
| 0 260 044 A1 | 3/1988 | European Pat. Off. . |
| 0578320A1 | 1/1994 | European Pat. Off. . |
| 0778007A1 | 6/1997 | European Pat. Off. . |
| 2 717 068 | 9/1995 | France . |
| 2732887A1 | 10/1996 | France . |
| 2736535A1 | 1/1997 | France . |
| 43 23 956 C1 | 7/1993 | Germany . |
| 1 424 826 A1 | 9/1988 | U.S.S.R. . |
| 97/00054 | 1/1997 | WIPO . |
| 97/06753 | 2/1997 | WIPO . |
| 98/14142 | 4/1998 | WIPO . |

OTHER PUBLICATIONS

Dialog Web results for search for English–language Abstract for SU1424826 published Sep. 23, 1988, downloaded and printed from www.dialogweb.com on Jan. 22, 1999 (2 pages).

(List continued on next page.)

*Primary Examiner*—David J. Isabella
*Attorney, Agent, or Firm*—Conley, Rose & Tayon PC

[57] ABSTRACT

Method and apparatus for promoting a spinal fusion between neighboring vertebrae. The apparatus may be located in an intervertebral disc space and the apparatus preferably includes a pair of engaging plates for contacting the vertebrae. An alignment device of the apparatus may be used to alter the vertical distance between the engaging plates to customize the apparatus to fit a given patient. In an embodiment, the alignment device includes a rotatable connector and cam pins for adjusting the distance between the engaging plates. The alignment device is preferably adapted to vary the distance between the engaging plates such that the height of the apparatus proximate the anterior end is greater than the height of the apparatus proximate the posterior end whereby the natural lordosis of the spine is maintained after the apparatus is installed. The apparatus may further include a load-sharing member to allow stress to be imparted to bone in the vicinity of the apparatus to promote bone growth in accordance with Wolff's law.

29 Claims, 11 Drawing Sheets

U.S. PATENT DOCUMENTS

| | | |
|---|---|---|
| 5,026,373 | 6/1991 | Ray et al. . |
| 5,047,029 | 9/1991 | Aebi et al. . |
| 5,055,104 | 10/1991 | Ray . |
| 5,074,864 | 12/1991 | Cozad et al. . |
| 5,102,412 | 4/1992 | Rogozinski . |
| 5,108,399 | 4/1992 | Eitenmuller et al. . |
| 5,108,446 | 4/1992 | Wagner et al. . |
| 5,116,340 | 5/1992 | Songer et al. . |
| 5,123,926 | 6/1992 | Pisharodi . |
| 5,127,912 | 7/1992 | Ray et al. . |
| 5,129,388 | 7/1992 | Vignaud et al. . |
| 5,129,904 | 7/1992 | Illi . |
| 5,147,359 | 9/1992 | Cozad et al. . |
| 5,154,718 | 10/1992 | Cozad et al. . |
| 5,171,278 | 12/1992 | Pisharodi . |
| 5,176,678 | 1/1993 | Tsou . |
| 5,176,680 | 1/1993 | Vignaud et al. . |
| 5,181,917 | 1/1993 | Rogozinski . |
| 5,192,321 | 3/1993 | Strokon . |
| 5,192,327 | 3/1993 | Brantigan et al. . |
| 5,201,734 | 4/1993 | Cozad et al. . |
| 5,242,445 | 9/1993 | Ashman . |
| 5,242,448 | 9/1993 | Pettine et al. . |
| 5,246,442 | 9/1993 | Ashman et al. . |
| 5,261,909 | 11/1993 | Sutterlin et al. . |
| 5,263,953 | 11/1993 | Bagby . |
| 5,281,222 | 1/1994 | Allard et al. . |
| 5,282,801 | 2/1994 | Sherman . |
| 5,290,312 | 3/1994 | Kojimoto et al. . |
| 5,290,494 | 3/1994 | Coombes et al. . |
| 5,303,718 | 4/1994 | Krajicek . |
| 5,304,179 | 4/1994 | Wagner . |
| 5,306,307 | 4/1994 | Senter et al. . |
| 5,306,309 | 4/1994 | Wagner et al. . |
| 5,312,405 | 5/1994 | Korotko et al. . |
| 5,312,410 | 5/1994 | Miller et al. . |
| 5,318,566 | 6/1994 | Miller . |
| 5,336,223 | 8/1994 | Rogers . |
| 5,336,240 | 8/1994 | Metzler et al. . |
| 5,344,422 | 9/1994 | Frigg . |
| 5,348,026 | 9/1994 | Davidson . |
| 5,357,983 | 10/1994 | Mathews . |
| 5,360,429 | 11/1994 | Jeanson et al. . |
| 5,360,431 | 11/1994 | Puno et al. . |
| 5,361,766 | 11/1994 | Nichols et al. . |
| 5,364,399 | 11/1994 | Lowery et al. . |
| 5,380,325 | 1/1995 | Lahille et al. . |
| 5,385,583 | 1/1995 | Cotrel . |
| 5,390,683 | 2/1995 | Pisharodi . |
| 5,395,374 | 3/1995 | Miller et al. . |
| 5,397,364 | 3/1995 | Kozak et al. . |
| 5,403,315 | 4/1995 | Ashman . |
| 5,405,391 | 4/1995 | Hednerson et al. . |
| 5,415,658 | 5/1995 | Kilpela et al. . |
| 5,417,690 | 5/1995 | Sennett et al. . |
| 5,423,820 | 6/1995 | Miller et al. . |
| 5,423,825 | 6/1995 | Levine . |
| 5,425,772 | 6/1995 | Brantigan . |
| 5,443,514 | 8/1995 | Steffee . |
| 5,466,237 | 11/1995 | Byrd, III et al. . |
| 5,474,555 | 12/1995 | Puno et al. . |
| 5,480,437 | 1/1996 | Draenert . |
| 5,484,437 | 1/1996 | Michelson . |
| 5,489,307 | 2/1996 | Kuslich et al. . |
| 5,489,308 | 2/1996 | Kuslich et al. . |
| 5,496,318 | 3/1996 | Howland et al. . |
| 5,505,732 | 4/1996 | Michelson . |
| 5,507,746 | 4/1996 | Lin . |
| 5,514,180 | 5/1996 | Heggeness et al. . |
| 5,520,690 | 5/1996 | Errico et al. . |
| 5,522,899 | 6/1996 | Michelson . |
| 5,527,341 | 6/1996 | Gogolewski et al. . |
| 5,531,746 | 7/1996 | Errico et al. . |
| 5,531,751 | 7/1996 | Schultheiss et al. . |
| 5,536,270 | 7/1996 | Songer et al. . |
| 5,536,271 | 7/1996 | Daly et al. . |
| 5,545,165 | 8/1996 | Biedermann et al. . |
| 5,549,608 | 8/1996 | Errico et al. . |
| 5,549,612 | 8/1996 | Yapp et al. . |
| 5,554,157 | 9/1996 | Errico et al. . |
| 5,563,124 | 10/1996 | Damien et al. . |
| 5,569,248 | 10/1996 | Mathews . |
| 5,569,253 | 10/1996 | Farris et al. . |
| 5,571,192 | 11/1996 | Schönhöffer . |
| 5,575,792 | 11/1996 | Errico et al. . |
| 5,578,033 | 11/1996 | Errico et al. . |
| 5,584,834 | 12/1996 | Errico et al. . |
| 5,586,984 | 12/1996 | Errico et al. . |
| 5,593,409 | 1/1997 | Michelson . |
| 5,601,553 | 2/1997 | Trebing et al. . |
| 5,601,556 | 2/1997 | Pisharodi . |
| 5,603,713 | 2/1997 | Aust et al. . |
| 5,607,424 | 3/1997 | Tropiano . |
| 5,607,425 | 3/1997 | Rogozinski . |
| 5,607,426 | 3/1997 | Ralph et al. . |
| 5,607,430 | 3/1997 | Bailey . |
| 5,609,592 | 3/1997 | Brumfield et al. . |
| 5,609,593 | 3/1997 | Errico et al. . |
| 5,609,594 | 3/1997 | Errico et al. . |
| 5,609,596 | 3/1997 | Pepper . |
| 5,609,635 | 3/1997 | Michelson . |
| 5,609,636 | 3/1997 | Kohrs et al. . |
| 5,611,800 | 3/1997 | Davis et al. . |
| 5,611,801 | 3/1997 | Songer . |
| 5,613,967 | 3/1997 | Engelhardt et al. . |
| 5,616,144 | 4/1997 | Yapp et al. . |
| 5,620,443 | 4/1997 | Gertzbein et al. . |
| 5,624,441 | 4/1997 | Sherman et al. . |
| 5,626,579 | 5/1997 | Muschler et al. . |
| 5,628,740 | 5/1997 | Mullane . |
| 5,628,756 | 5/1997 | Barker, Jr. et al. . |
| 5,630,816 | 5/1997 | Kambin . |
| 5,632,747 | 5/1997 | Scarborough et al. . |
| 5,634,925 | 6/1997 | Urbanski . |
| 5,643,260 | 7/1997 | Doherty . |
| 5,643,264 | 7/1997 | Sherman et al. . |
| 5,643,265 | 7/1997 | Errico et al. . |
| 5,645,084 | 7/1997 | McKay . |
| 5,645,544 | 7/1997 | Tai et al. . |
| 5,645,549 | 7/1997 | Boyd et al. . |
| 5,645,598 | 7/1997 | Brosnahan, III . |
| 5,647,873 | 7/1997 | Errico et al. . |
| 5,649,927 | 7/1997 | Kilpela et al. . |
| 5,651,283 | 7/1997 | Runciman et al. . |
| 5,651,789 | 7/1997 | Cotrel . |
| 5,653,708 | 8/1997 | Howland . |
| 5,653,709 | 8/1997 | Frigg . |
| 5,653,763 | 8/1997 | Errico et al. ............................... 623/17 |
| 5,658,289 | 8/1997 | Boucher et al. . |
| 5,658,335 | 8/1997 | Allen ........................................ 623/17 |
| 5,658,337 | 8/1997 | Kohrs et al. . |
| 5,658,516 | 8/1997 | Eppley et al. . |
| 5,662,653 | 9/1997 | Songer et al. . |
| 5,665,088 | 9/1997 | Gil et al. . |
| 5,665,112 | 9/1997 | Thal . |
| 5,665,122 | 9/1997 | Kambin . |
| 5,667,506 | 9/1997 | Sutterlin . |
| 5,667,507 | 9/1997 | Corin et al. . |
| 5,667,508 | 9/1997 | Errico et al. . |
| 5,668,288 | 9/1997 | Storey et al. . |
| 5,669,909 | 9/1997 | Zdeblick et al. . |
| 5,669,910 | 9/1997 | Korhonen et al. . |

| | | |
|---|---|---|
| 5,669,911 | 9/1997 | Errico et al. . |
| 5,671,695 | 9/1997 | Schroeder . |
| 5,672,175 | 9/1997 | Martin . |
| 5,672,176 | 9/1997 | Biedermann et al. . |
| 5,674,222 | 10/1997 | Berger et al. . |
| 5,674,295 | 10/1997 | Ray et al. . |
| 5,674,296 | 10/1997 | Bryan et al. . |
| 5,676,665 | 10/1997 | Bryan . |
| 5,676,666 | 10/1997 | Oxland et al. . |
| 5,676,701 | 10/1997 | Yuan et al. . |
| 5,676,703 | 10/1997 | Gelbard . |
| 5,681,311 | 10/1997 | Foley et al. . |
| 5,681,312 | 10/1997 | Yuan et al. . |
| 5,683,391 | 11/1997 | Boyd . |
| 5,683,392 | 11/1997 | Richelsoph et al. . |
| 5,683,393 | 11/1997 | Ralph . |
| 5,683,394 | 11/1997 | Rinner . |
| 5,688,272 | 11/1997 | Montague et al. . |
| 5,688,273 | 11/1997 | Errico et al. . |
| 5,688,274 | 11/1997 | Errico et al. . |
| 5,688,279 | 11/1997 | McNulty et al. . |
| 5,688,280 | 11/1997 | Booth, Jr. et al. . |
| 5,690,629 | 11/1997 | Asher et al. . |
| 5,690,630 | 11/1997 | Errico et al. . |
| 5,690,631 | 11/1997 | Duncan et al. . |
| 5,690,632 | 11/1997 | Schwartz et al. . |
| 5,690,633 | 11/1997 | Taylor et al. . |
| 5,690,842 | 11/1997 | Panchison . |
| 5,693,046 | 12/1997 | Songer et al. . |
| 5,693,053 | 12/1997 | Estes . |
| 5,693,100 | 12/1997 | Pisharodi . |
| 5,697,929 | 12/1997 | Mellinger . |
| 5,697,977 | 12/1997 | Pisharodi . |
| 5,700,291 | 12/1997 | Kuslich et al. . |
| 5,700,292 | 12/1997 | Margulies . |
| 5,702,391 | 12/1997 | Lin . |
| 5,702,392 | 12/1997 | Wu et al. . |
| 5,702,393 | 12/1997 | Pfaifer . |
| 5,702,394 | 12/1997 | Henry et al. . |
| 5,702,395 | 12/1997 | Hopf . |
| 5,702,396 | 12/1997 | Hoenig et al. . |
| 5,702,399 | 12/1997 | Kilpela et al. . |
| 5,702,449 | 12/1997 | McKay . |
| 5,702,450 | 12/1997 | Bisserie . |
| 5,702,451 | 12/1997 | Biedermann et al. . |
| 5,702,452 | 12/1997 | Argenson et al. . |
| 5,702,453 | 12/1997 | Rabbe et al. . |
| 5,702,454 | 12/1997 | Baumgartner . |
| 5,702,455 | 12/1997 | Saggar . |
| 5,704,936 | 1/1998 | Mazel . |
| 5,704,937 | 1/1998 | Martin . |
| 5,707,372 | 1/1998 | Errico et al. . |
| 5,707,395 | 1/1998 | Li . |
| 5,709,681 | 1/1998 | Pennig . |
| 5,709,682 | 1/1998 | Medoff . |
| 5,709,683 | 1/1998 | Bagby . |
| 5,709,684 | 1/1998 | Errico et al. . |
| 5,709,685 | 1/1998 | Dombrowski et al. . |
| 5,709,686 | 1/1998 | Talos et al. . |
| 5,713,841 | 2/1998 | Graham . |
| 5,713,898 | 2/1998 | Stucker et al. . |
| 5,713,899 | 2/1998 | Marnay et al. . |
| 5,713,900 | 2/1998 | Benzel et al. . |
| 5,713,903 | 2/1998 | Sander et al. . |
| 5,713,904 | 2/1998 | Errico et al. . |
| 5,716,355 | 2/1998 | Jackson . |
| 5,716,356 | 2/1998 | Biedermann et al. . |
| 5,716,357 | 2/1998 | Rogozinski . |
| 5,716,358 | 2/1998 | Ochoa et al. . |
| 5,716,359 | 2/1998 | Ojima et al. . |
| 5,716,415 | 2/1998 | Steffee . |
| 5,716,416 | 2/1998 | Lin . |
| 5,720,746 | 2/1998 | Soubeiran . |
| 5,720,747 | 2/1998 | Burke . |
| 5,720,748 | 2/1998 | Kuslich et al. . |
| 5,720,751 | 2/1998 | Jackson . |
| 5,722,977 | 3/1998 | Wilhelmy . |
| 5,749,916 | 5/1998 | Richelsoph . |
| 5,782,832 | 7/1998 | Larsen et al. . |
| 5,782,919 | 7/1998 | Zdeblick et al. . |
| 5,785,710 | 7/1998 | Michelson . |

OTHER PUBLICATIONS

Dialog Web results for search for English–language Abstract for DE 4323956 published Jul. 19, 1993, downloaded and printed from www.dialogweb.com on Jan. 22, 1999 (2 pages).

Dialog Web results for search for English–language Abstract for FR 2717068 published Sep. 15, 1995, downloaded and printed from www.dialogweb.com on Jan. 22, 1999 (1 page).

International Search Report for PCT/US 98/08832 dated Sep. 1, 1998.

Danek Group, Inc. Medical Division Publication entitled, "TSRH Spinal System—Unmatched versatility," pp. 1–4.

Danek Surgical Technique Manual entitled, "TSRH Spinal Implant System, " Date Unknown, pp. 1–16.

Danek Surgical Technique Manual entitled, "TSRH Crosslink," Date Unknown, pp. 1–8.

Dickman Curtis A., et al., BNI Quarterly Publication entitled, "Techniques of Screw Fixation of the Cervical Spine," vol. 9, No. 4, Fall 1993, pp. 27–39.

Slone et al., RadioGraphics Publication entitled, "Spinal Fixation," vol. 13, No. 2, Mar. 1993, pp. 341–356.

Synthes Spine Publication entitled, "The Universal Spinal System—Internal Fixation for the Spine," 1994, pp. 1–15.

AcroMed Publication entitled, "The ISOLA Spinal System—Versatility, simplicity and minimal profile in the surgical treatment of the spine," 1994, pp. 1–15.

AcroMed Corporation Publication entitled, "ISOLA® Transverse Rod Connectors: Principles and Techniques," Date Unknown, pp. i, ii, 1–8.

Danek Publication entitles, "AXIS—Fixation System, " 1993, pp. 1–6.

Synthes Publication entitled, "Small Notched Titanium Reconstruction Plate System," 1996, pp. 1–6.

J. Neurosurg Publication entitled, "Posterior plates in the management of cervical instability: long–term results in 44 patients," vol. 81, 1994, pp. 341–349.

BNI Quarterly Publication entitled, "Lateral Mass Posterior Plating and Facet Fusion for Cervical Spine Instability," vol. 7, No. 2, 1991, pp. i, ii, 1–12.

Beadling, Lee, Orthopedics Today Publication entitled, "FDA Clears Spinal Cages for Interbody Lumbar Fusion," pp. 1–2.

MedPro Month Publication entitled, "Trends in Spine & Disk Surgery," vol. vo, No. 11–12, PP. 280–284.

Surgical Dynamics Ray Threaded Fusion Cage Device Surgical Technique Manual, pp. 1–10.

Surgical Dynamics Ray Threaded Fusion Cage, pp. 1–6.

AcroMed Publication entitled, "AcroMed Spinal Solutions for Cervical Pathologies," 07–95, pp. 1–8.

Codman Publication entitled, "Sof'wire Cable System," 6 pp.

Huhn, Stephen L. et al., "Posterior Spinal Osteosynthesis for Cervical Fracture/Dislocation Using a Flexible Multistrand Cable System: Technical Note," Neurosurgery, vol. 29, No. 6, 1991, pp. 943–946.

Dickman, Curtis A. et al., "Wire Fixation for the Cervical Spine: Biomechanical Principles and Surgical Techniques," BNI Quarterly, vol. 9, No. 4, Fall 1993, pp. 2–16.

Publication by AcroMed entitled, "ACROMED Cable System by Songer,"Sep. 1993, 4 pp.

M. Aebi, MD, et al., "Treatment of Cervical Spine Injuries with Anterior Plating: Indications, Techniques, and Results," vol. 16, No. 3S, Mar., 1991 Supplement, pp. S38–S45.

Foley, M.D. et al., "Aline Anterior Cervical Plating System," Smith & Nephew Richards, Inc. Orthopaedics Catalog Information, Sep. 1996, pp. 1–16.

Lowery, Gary L., M.D., Ph.D., Sofamor Danek Group, Inc. Publication entitled, "Orion Anterior Cervical Plate System: Surgical Technique," 1994, pp. 1–24.

Apfelbaum, R., M.D., Aesculap Scientific Information publication entitled, "Posterior Trnasarticular C1–2 Screw Fixation for Atlantoaxial Instability," 1993, pp. 1–15.

Danek Titanium Cable System publication by Danek Group, Inc., 1994, 6 pp.

Publication entitled,"Spinal Disorders", 4 pp.

O'Brien, John P., Ph.D., Orthopaedic Product News Article entitled, "Interbody Fusion of the Lumbar Spine," pp. 1–3.

Roy et al., "Variation of Young's Modulus and Hardness in Human Lumbar Vertebrae Measured by Nanoindentation", pp. 1–4.

Sofamor Danek publication entitled, "Atlas Cable System: Evolution of the Cable System for Spinal Applications," 1995, 2 pp.

AcroMed publication entitled, "AcroMed Songer Cable System: Ordering information for Implants and Instruments," Apr. 1996, 4 pp.

Songer, Matthew, M.D., "Acromed Cable System by Songer: Cervical Technique Manual," pp. 1–17.

Songer, Matthew N., M.D., "ACROMED Cable System by Songer: Technique Manual," 1993, pp. 1–20.

Oxland, Thomas R., Ph.D., et al., SpineTech Inc. Publication entitled, "Biomechanical Rationale—The BAK Interbody Fusion System: An Innovative Solution," pp. 1–16.

SpineTech, Inc. publication entitled, "Patient Information on Spinal Fusion Surgery and the BAK Interbody Fusion System," 10 pp.

SpineTech, Inc. publication entitled, "BAK/Cervical Interbody Fusion System," 1994, 2 pp.

SpineTech, Inc. publications entitled, "Instrumentation BAK Interbody Fusion System," "Biomechanics BAK Interbody Fusion System," and "Porosity BAK Interbody Fusion System," 1996, 12 pp.

SpineTech, Inc. publication entitled, "The BAK Interbody Fusion System," 1996, 4 pp.

Depuy Motech, Inc. publication entitled, "Moss Miami 3–Dimensional Spinal Instrumentation: Taking Spinal Instrumentation to a New Dimension," 19*95, 8 pp.

Shufflebarger, Harry L., M.D., "Moss Miami Spinal Instrumentation System: Methods of Fixation of the Spondylopelvic Junction," *Lumbosacral and Spinopelvic Fixation*, 1996 by Raven Publishers, Philadelphia, pp. 381–393.

Shufflebarger, Harry L., M.D., Depuy Motech publication entitled, "Clinical Issue: Rod Rotation in Scoliosis Surgery," 5 pp.

AcroMed publication entitled, "Instruments," 3 pp.

SpineTech, Inc. publication entitled, "The Bone Harvester," 1996, 2 pp.

Wright Medical Technology Publication entitled, "Versalok Low Back Fixation System," 1996, pp. 1–4.

Danek Medical, Inc. Publication entitled, "TSRH Lumbar System," 1991, pp. 1–4.

Spinal Concepts Inc. publication entitled "The BacFix ss—Posterior Lower Back Fixation System–Written Surgical Technique," 1997, pp. 1–11.

International Search Report PCT/US 97/16971 dated Feb. 6, 1998.

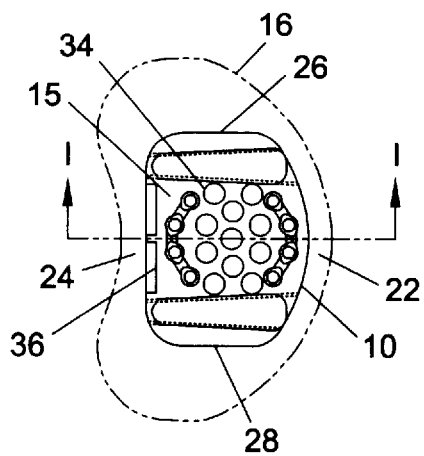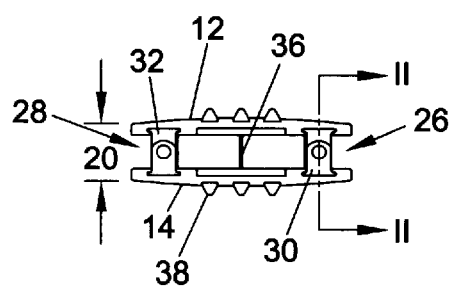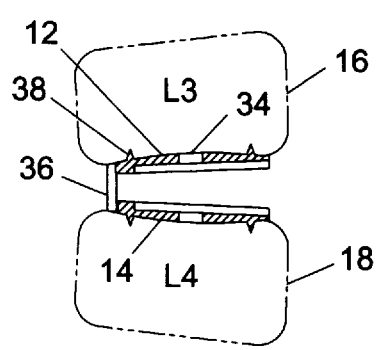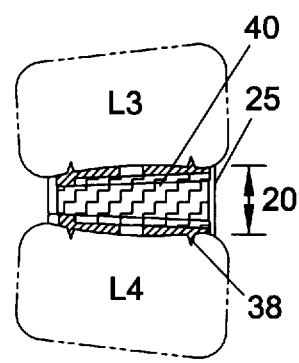
FIG. 3  FIG. 5
FIG. 4A  FIG. 4B

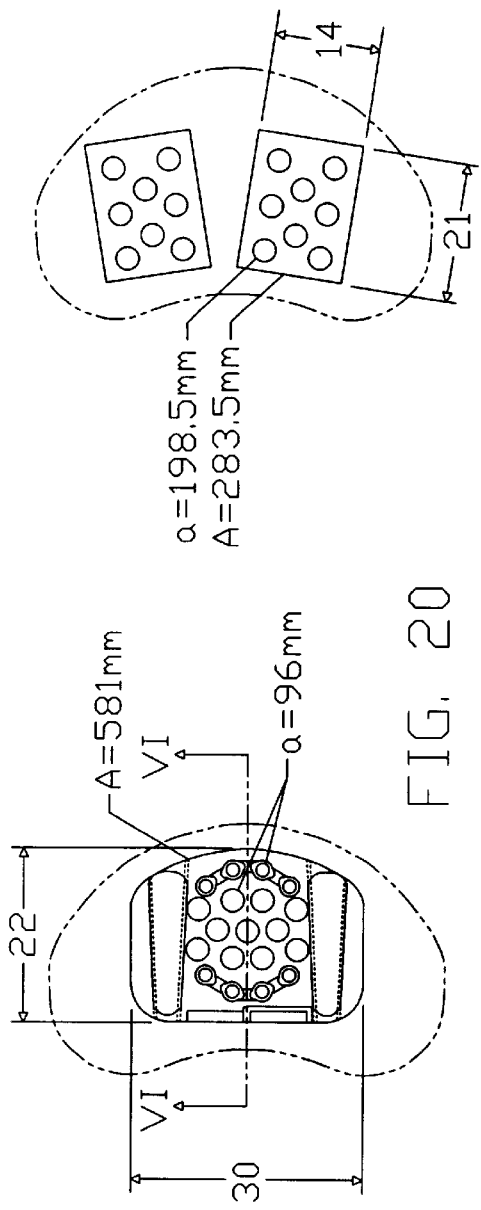
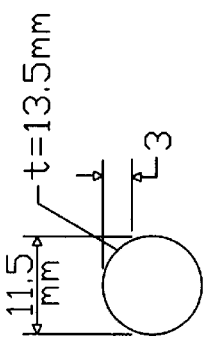
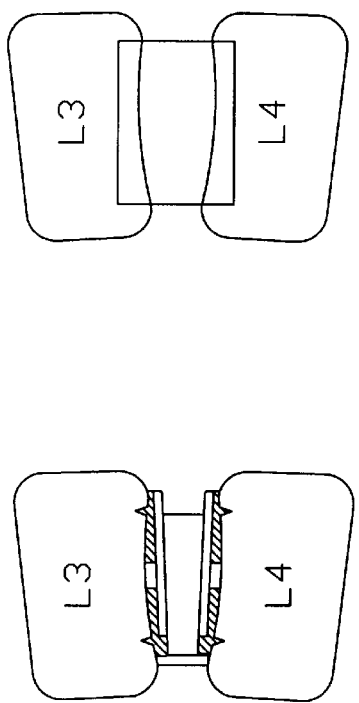
FIG. 20
FIG. 22 (PRIOR ART)
FIG. 24 (PRIOR ART)
FIG. 23 (PRIOR ART)
FIG. 21

ADJUSTABLE HEIGHT FUSION DEVICE

This is a divisional of copending application Ser. No. 08/847,172 filed May 1, 1997.

BACKGROUND OF THE INVENTION

1. Field of the Invention

The present invention generally relates to methods and apparatus for promoting an intervertebral fusion, and more particularly to an apparatus for insertion into a space between adjacent vertebrae to facilitate an intervertebral fusion while maintaining a substantially natural lordosis of the human spine.

2. Description of the Related Art

Intervertebral discs that become degenerated due to various factors such as trauma or aging typically have to be partially or fully removed. Removal of an intervertebral disc can destabilize the spine, making it necessary to replace the vertebral disc to maintain the height of the spine and to fuse the spine. Spinal implants are often used to prevent collapse of the spine. U.S. Ser. No. 08/740,123 filed Oct. 24, 1996 relates to methods and apparatus for facilitating a spinal fusion and is incorporated by reference as if fully set forth herein.

After an intervertebral disc is removed, an implant device is typically inserted between neighboring vertebrae to maintain normal disc spacing and restore spinal stability, thereby facilitating an intervertebral fusion. A conventional implant device disposed between neighboring vertebrae is depicted in FIGS. 1 and 2. The implant device contains a pair of engaging elements 20 that typically contain threading 10 to engage the vertebrae. Prior to inserting the engaging elements, a vertebral drill is typically inserted within the surgical wound to drill into the cortical endplate and remove fibrous and nuclear material. A vertebral tap may then be used to cut threads into the ends of the neighboring vertebrae. The engaging elements tend to be relatively inflexible and substantially undeflectable. The engaging elements are typically packed with bone graft to facilitate a spinal fusion.

Conventional implant devices tend to not maintain the "lordosis" or natural curvature of the lower lumbar spine. As shown in FIG. 1, the implant device contains parallel engaging sides 12 and 13 to contact vertebra 15. It is typically required that the engaging sides be parallel to prevent the fusion cage from slipping from the intervertebral space. The parallel configuration of the fusion cage tends to alter the lordosis of the spine. Such a loss of lordosis may result in an increased risk to other intervertebral discs located adjacent to the fusion level that may degenerate due to the altered force transmission in the spine.

FIG. 2 depicts a front view of the engaging elements 20 of the implant device. The engaging elements are substantially cylindrical and the region of contact between an engaging element and a vertebra is defined by arcuate portion 22. The cylindrical geometry of the engaging elements tends to provide a relatively small area of contact between the fusion cage and the vertebrae. The weight of the spine creates pressure on the vertebrae that is concentrated proximate the arcuate portions. Subsidence or deformation of the cortical layer of the vertebrae tends to result.

U.S. Pat. No. 5,522,899 to Michelson relates to a spinal implant for placement into the spinal disc space to stabilize the spine and participate in a vertebra to vertebra bony fusion. U.S. Pat. No. 5,489,308 to Kuslich et al. relates to an implant for use in spinal stabilization that includes a cylindrical body having external threading and radially disposed openings positioned to chip bone into an interior portion of the body when the implant is installed. The above-mentioned patents are incorporated by reference as if fully set forth herein.

The above-mentioned prior methods and systems inadequately address, among other things, the need to maintain the natural lordosis of the spine. It is therefore desirable that an improved spinal implant be derived for facilitating an intervertebral body fusion.

SUMMARY OF THE INVENTION

In accordance with the present invention, a spinal implant is provided that largely eliminates or reduces the aforementioned disadvantages of conventional implant devices. An embodiment of the invention relates to a fusion device for facilitating an interbody fusion between neighboring vertebrae of a human spine. The fusion device preferably includes a pair of sides or engaging plates for engaging the vertebrae and an alignment device disposed between the engaging plates for separating the engaging plates to maintain the engaging plates in lordotic alignment. The alignment device is preferably adapted to adjust the height between the engaging plates to customize the fusion device to a particular patient. The height of the fusion device preferably varies along the length of the device such that the height proximate an anterior end of the device differs from the height proximate a posterior end of the device.

The engaging plates are preferably substantially planar so as to inhibit subsidence of the vertebrae. The engaging plates may contain protrusions extending from their outer faces for enhancing an engagement between the vertebra and the engaging plate. The protrusions may be adapted to extend into the vertebra. The engaging plates preferably include a plurality of openings to allow bone growth to occur through the engaging plates. The openings in the face of the engaging plates preferably have a total area that is between about 60 percent and about 80 percent of a total surface area of the face (including the area of the openings).

The fusion device may include a retaining plate proximate the posterior end that serves as a backing against which bone graft may be packed between the engaging plates. The fusion device may also include a removable end cap proximate the anterior end for maintaining bone graft between the engaging plates.

In an embodiment, the alignment device includes a first strut and a second strut that each extend between the engaging plates to define the height therebetween. The fusion device preferably includes a first side and a second side opposite the first side. The first strut preferably runs from the anterior end to the posterior end along a location proximate the first side, and the second strut preferably runs from the anterior end to the posterior end along a location proximate the second side. The engaging plates preferably include a pair of slots sized to receive ends of the struts. The slots may have a substantially dovetail-shaped cross-section that is conformed to the shape of the ends. Each slot is preferably tapered such that its width narrows in a direction from the anterior end to the posterior end whereby the width of the slot proximate the posterior end is less than the width of the end of the strut. The ends of the struts preferably have a lateral width that tapers in substantially the same manner as the slots such that a locking taper engagement is formable between the slots and the ends of the struts.

The height of each strut preferably varies along the length of the strut such that the height between the engaging plates differs between the anterior end and the posterior end to allow the lordosis of the spine to be maintained. The first and second struts may have differing heights to cause the height of the fusion device to vary along the device from the first side to the second side to correct for a lateral deviation in the spinal column. Each of the struts may include a hinge to allow an upper member of the strut to pivot with respect to a lower member of the strut.

In an alternate embodiment, the engaging plates include slots and the fusion device further includes a pair of pins disposed within the slots. Each engaging plate preferably includes a rib extending in a substantially perpendicular direction from its face. The slot for receiving the pins is preferably disposed on the rib. The pins are preferably substantially elongated and may extend in a direction from the first side to the second side. The fusion device preferably further includes a rotatable connector engaging the pins. Rotation of the connector preferably causes movement of the pins relative to one another to alter the height of the fusion device to create a desired lordotic alignment.

The connector is preferably adapted to move axially between the engaging plates and may contain a retaining ring for contacting an engaging plate to limit movement of the connector through the fusion device. The connector preferably moves axially between the engaging plates in a direction from the anterior end to the posterior end, thereby moving the first pin toward the anterior end and the second pin toward the posterior end to increase the height between the engaging plates. The connector may be a screw having a threaded portion. The first pin may include a threaded opening for receiving a threaded portion of the connector. The second pin may be connected to an unthreaded portion of the connector.

The pins preferably include a receiving section and an end. The ends of the pins are preferably sized to fit within the slots in the ribs of the engaging plates. The receiving section may have a width greater than that of the ends of the pins and preferably contains an opening for receiving the connector.

One engaging plate preferably includes a first slot that may terminate in an end that extends in a diverging direction from an end of another slot contained on the other engaging plate. Movement of one of the pins preferably draws the ends of the slots together to alter the amount of separation between the engaging plates. The movement of the pins relative to one another preferably alters the height proximate the anterior end at a faster rate than the height proximate the posterior end is altered to achieve a desired lordotic alignment.

In an alternate embodiment, the fusion device contains a load-sharing member to promote a spinal fusion. The load-sharing member may be axially disposed within the struts. The load-sharing member is preferably substantially deflectable to allow movement of one of the engaging plates when a compressive force is exerted on the engaging plates. A predetermined spacing preferably exists between the upper and lower members. Application of a compressive force onto the engaging plates preferably deflects the load-sharing member and decreases the predetermined spacing, between the members, thereby decreasing the height of the strut. The deflection of the load-sharing member preferably imparts stress to bone graft proximate the engaging plates to promote the development and growth of bone in accordance with Wolff's law.

The load-sharing member may be a pin having a circular cross-section and preferably is disposed in a bore extending axially through the strut. The bore preferably has a greater width than that of the load-sharing member to provide space for deflection of the load-sharing member. The load-sharing member may serve as a hinge-pin about which the upper member of the strut pivots with respect to the lower member of the strut.

The fusion device preferably further includes a connector for engaging the load-sharing member to impart force to the load-sharing member to cause it to deflect. The strut may include a threaded opening in its end for receiving the connector. The predetermined spacing between the upper and lower members may be set to a desired length by altering the position of the connector in the opening in the end of the strut. The load-sharing member may include an indention having a substantially planar surface to provide a site for engagement with the connector. The connector preferably engages the load-sharing member at a fulcrum point located at a predetermined horizontal distance from a support location where the lower member of the strut contacts the load-sharing member. The material properties of the load-sharing member and the distance between the fulcrum point and the support location are preferably controlled such that the modulus of elasticity across the strut is substantially equal to the modulus of elasticity of bone.

The above embodiments may be used independently or in combination.

An advantage of the invention relates to an intervertebral body fusion device that substantially maintains the natural lordosis of the human spine.

Another advantage of the invention relates to an intervertebral body fusion device adapted to correct a lateral deviation in the spinal column.

Another advantage of the invention relates to an intervertebral body fusion device adapted to deflect to impart stress on surrounding bone to promote bone growth.

BRIEF DESCRIPTION OF THE DRAWINGS

Further advantages of the present invention will become apparent to those skilled in the art with the benefit of the following detailed description of the preferred embodiments and upon reference to the accompanying drawings in which:

FIG. 3 depicts a top view of a fusion device located on a vertebral body.

FIG. 4a depicts a cross-sectional view of the fusion device of FIG. 3 taken along plane I.

FIG. 4b depicts a cross-sectional view of the fusion of FIG. 3 device taken along plane I wherein the fusion device contains bone graft and has been adjusted to maintain a substantially natural lordosis.

FIG. 5 depicts a front view of a fusion device.

FIG. 20 depicts a top view of a fusion device located on a vertebral body.

FIG. 21 depicts a cross-sectional view of the fusion device taken along plane VI of FIG. 3.

FIG. 22 depicts a top view of a conventional fusion cage having a pair of cylindrical elements disposed on a vertebra.

FIG. 23 depicts a side view of one of the cylindrical elements in FIG. 22 disposed between neighboring vertebrae.

FIG. 24 depicts a front view of the cylindrical element in FIG. 23.

Figure 1:
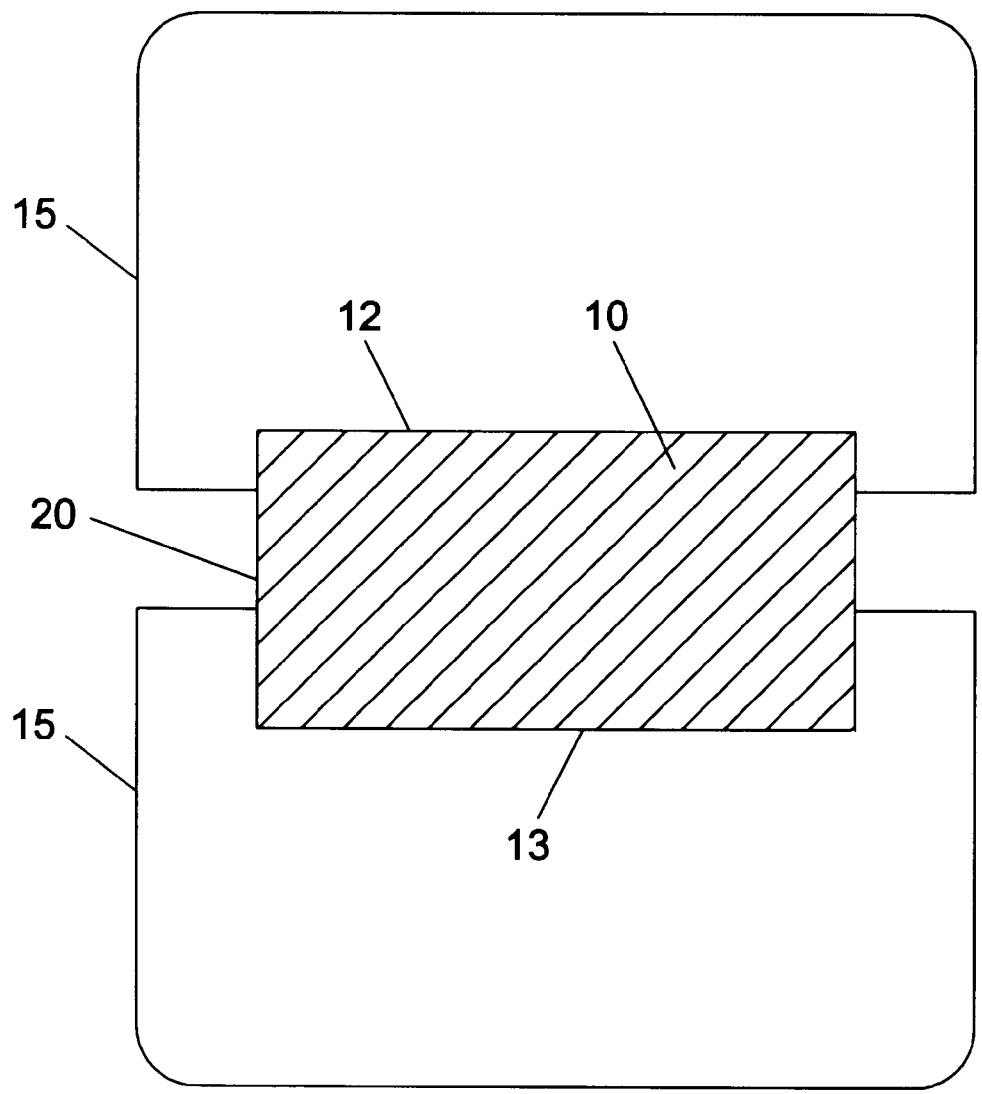
FIG. 1 depicts a conventional intervertebral body fusion implant positioned between neighboring vertebrae.
Figure 2:
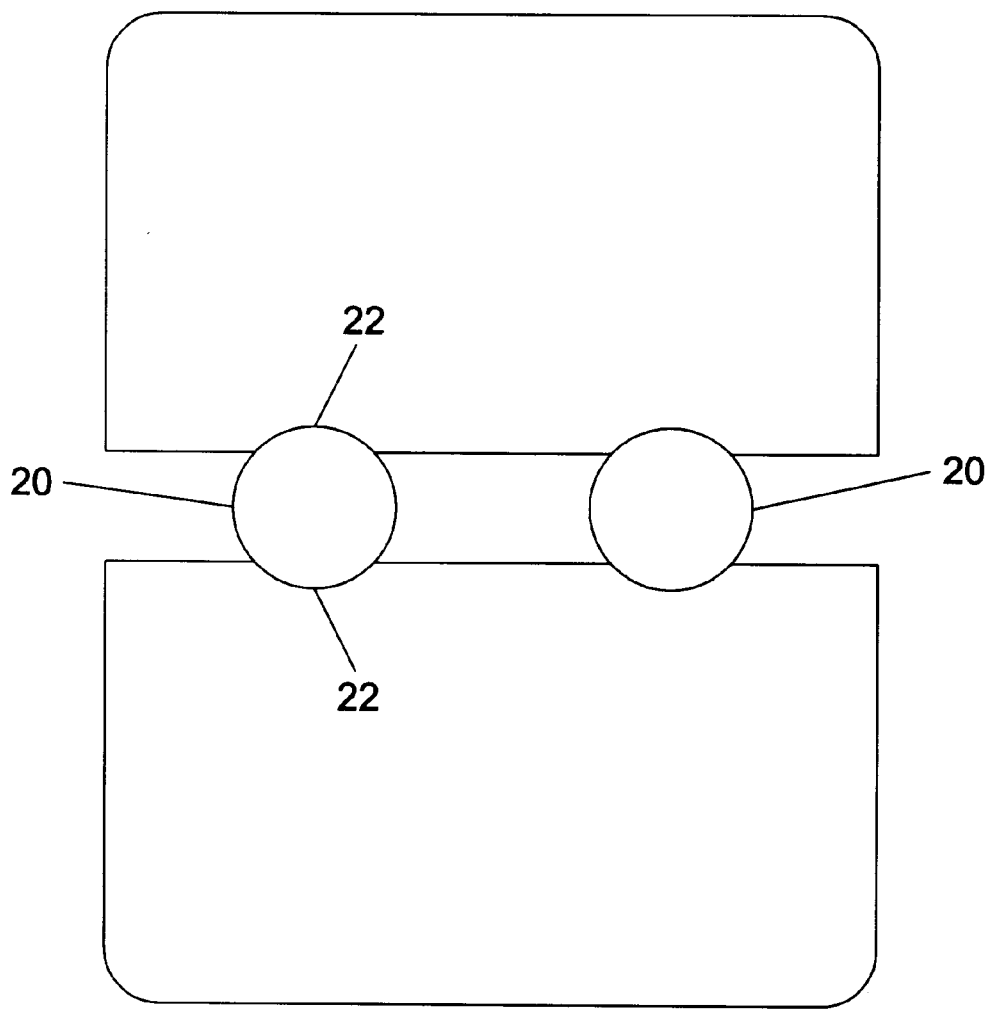
FIG. 2 depicts another conventional intervertebral body fusion implant that includes a pair of cylindrical members positioned between neighboring vertebrae.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

A preferred embodiment of an interbody fusion implant device 10 for facilitating the formation of a spinal fusion is depicted in FIGS. 3–5. A top view of the fusion device is depicted in FIG. 3. Fusion device 10 preferably includes a pair of sides or engaging plates 12 and 14 for engaging vertebral bodies 16 and 18. The engaging plates may contain curved edges such that the outer face 15 of the plates conforms to the shape of the cross-section of the vertebral bodies as shown in FIG. 3. The fusion device has a height 20 defined by the vertical distance between the outer faces 15 of the engaging plates 12 and 14. The height 20 of the fusion device is preferably adjustable and may vary along the fusion device between anterior end 22 and posterior end 24 to maintain the natural lordosis of the spine. Height 20 may also vary along device 10 from first side 26 to second side 28 to correct for a lateral deviation in the spine as may occur in scoliosis. Fusion device 10 preferably further includes an alignment device for adjusting the height 20 so that the natural lordosis of the spine is substantially maintained after the fusion device is implanted. The alignment device may be used to adjust the height between the engaging plates proximate the anterior end and independently adjust the height between the engaging plates proximate the posterior end.

A spinal fusion is typically employed to eliminate pain caused by the motion of degenerative disk material. Upon successful fusion, fusion device 10 becomes permanently fixed within the disc space. The fusion device is preferably packed with bone graft 40 to promote the growth or bone through and around the fusion device. Such bone graft may be packed between engaging plates 12 and 14 prior to, subsequent to, or during implantation of the fusion device. Bone substitute material that is well known to those skilled in the art may be used instead of bone graft. A bone harvester kit, commercially available from Spine-Tech, Inc. located in Minneapolis, Minn., may be used to inject bone graft between the engaging plates. The pamphlet entitled "Bone Harvester: Minimally Invasive Bone Harvesting Kit" (available from Spine-Tech, Inc.) details the use of the bone harvesting kit.

In an embodiment of the invention, the faces 15 of engaging plates 12 and 14 contain a plurality of openings 34 disposed therein to allow bone development and growth through the engaging plates 12 and 14 and between fusion device 10 and neighboring vertebrae 16 and 18. In an embodiment, the openings 34 have a combined area that is greater than about 50 percent of the area of face 15 (including the area of the openings 34), more preferably between about 60 percent and about 80 percent of the area of face 15, and more preferably still about 70 percent or more of the area of face 15.

The fusion device may contain a retaining plate 36 proximate posterior end 24 to provide a backing against which bone graft may be packed and to maintain the bone graft between the engaging plates. Retaining plate 36 may be substantially planar and may contain openings to allow bone ingrowth therethrough. A removable endcap 25 may be positioned proximate anterior end 22 to contain bone graft within the fusion device and to prevent the migration of bone graft outside the engaging plates. The endcap 25 may contain one or more openings for allowing bone ingrowth between a vertebral body and bone graft contained between the engaging plates. Endcap 25 is preferably made of a plastic material such as polyethylene that tends to be non-irritating and non-abrasive to the surrounding tissues.

A cross section of the fusion device taken through plane I of FIG. 3 is depicted in FIG. 4a and FIG. 4b. FIG. 4a shows the relative position of engaging plates 12 and 14 before height 20 has been adjusted with an alignment device to achieve a substantially natural lordosis. FIG. 4b shows the relative position of the plates after height 20 has been adjusted and bone graft 40 has been packed between the engaging plates. FIG. 4b shows that height 20 is greater in the vicinity of anterior end 22 as compared to posterior end 24 to maintain the natural lordosis of the spinal column. The faces 15 of the engaging plates 12 and 14 are preferably planar to provide a relatively large contact area between the engaging plates and the neighboring vertebrae. In this manner, subsidence of the vertebrae may be prevented because the force imparted to the vertebrae from the fusion device is not concentrated across a relatively small area of the vertebrae as in some conventional implants. Alternately, the engaging plates may be non-planar. The engaging plates also preferably contain a plurality of spikes or protrusions 38 extending from the face 15 for enhancing an engagement between the vertebra and the engaging plate. The protrusions may extend into the vertebra to prevent the fusion device from moving out of the disc space. The engaging plates are preferably constructed of titanium or a titanium alloy, although it is to be understood that other materials (e.g., ceramics, metals, carbon composites) may be used.

A front view of the fusion implant device is depicted in FIG. 5. In an embodiment of the invention, the alignment device includes a first strut 30 and a second strut 32 that each extend between engaging plates 12 and 13 along the length of the fusion device from anterior end 22 to posterior end 24. As described herein, a "strut" is taken to mean any support member disposed between the engaging plates to separate the engaging plates. Strut 30 preferably extends along the fusion device proximate first side 26. Strut 32 is preferably substantially parallel to strut 30 and may extend along the fusion device proximate second side 28. The struts 30 and 32 serve to create a predetermined spacing between the engaging plates. The predetermined spacing is preferably such that the height 20 is approximately equal to the height of the disc material that formerly occupied the disc space between the vertebral bodies.

Figure 6A:
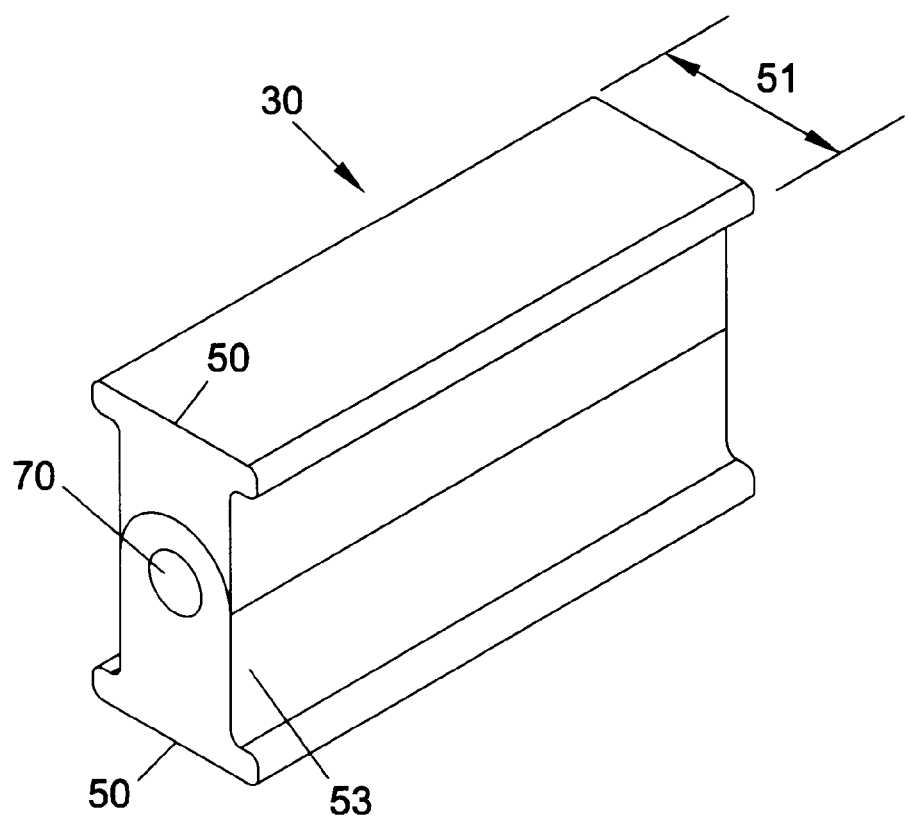
FIG. 6a depicts a perspective view of a strut.
Figure 8:
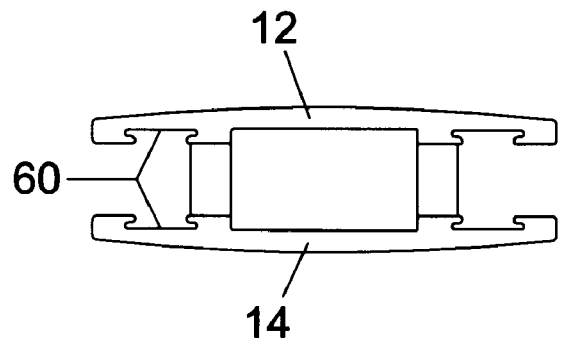
FIG. 8 depicts a front view of a pair of engaging plates.

A perspective view of an embodiment of the strut is depicted in FIG. 6a. The strut may have an "I-beam" shape and preferably includes a pair of ends 50. The ends 50 may have a lateral width 51 that is greater than that of the sides 53. The ends preferably have a "dovetail" shaped cross-section as shown in FIG. 6a. The engaging plates preferably contain elongated slots 60 (shown in FI(s. 7 and 8) sized to receive ends 50 of the first and second struts. The slots 60 preferably have a complementary dovetail shape as depicted in FIG. 8 that conforms to the shape of the end 50. The struts may be connected to the engaging plates by sliding ends 50 into the slots 60 in a direction from anterior end 22 to posterior end 24 or vice versa.

Figure 7:
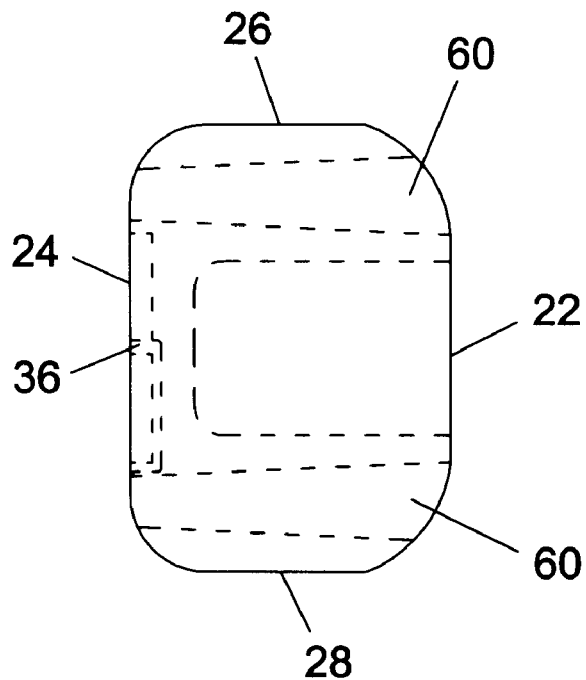
FIG. 7 depicts a top view of a fusion device.
Figure 17:
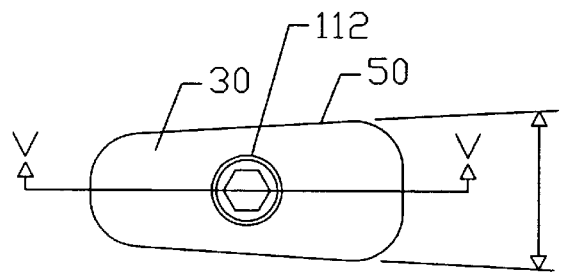
FIG. 17 depicts a top view of a strut having a tapered end.

In an embodiment, the slots are tapered such that their width narrows in a direction from the anterior end to the posterior end as shown in FIG. 7. The ends 50 may be tapered (as shown in FIG. 17) such that the lateral width 51 narrows along the length of the strut. The taper of the lateral width of the strut preferably matches that of slot 60. The width of the slot proximate the anterior end is preferably sized to allow the strut end to be slid into the slot. The width of the slot proximate the posterior end is preferably less than the lateral width 51 of the narrowest portion of end 50. The tapering of the slots preferably allows a "locking taper engagement" of the strut ends within the slots. A "locking taper engagement" is taken to mean a fixable interference fit formed between end 50 and slot 60 whereby the strut resists dislodgement when force is imparted to the fusion device from the adjacent vertebrae. In an alternate embodiment, the slots may be tapered such that the width of the slots narrows in a direction from the posterior end to the anterior end.

Figure 6B:
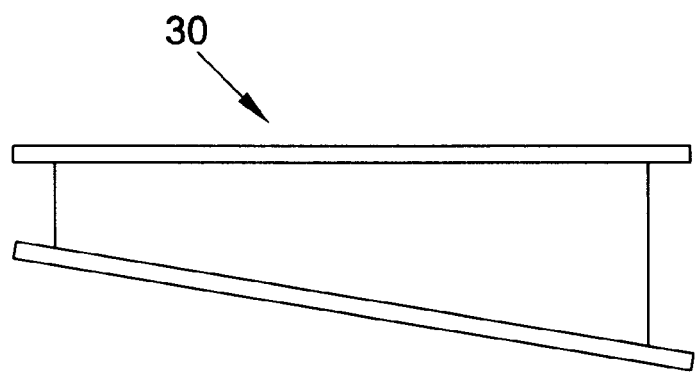
FIG. 6b depicts a side view of a tapered strut.

The first and second struts preferably each have a predetermined height that defines the height of the fusion device. The engaging plates 12 and 14 are preferably adapted to receive struts of various heights to allow height 20 to be varied to fit the needs of the patient. A side view of a tapered strut is depicted in FIG. 6b. The tapered strut preferably has a height that varies along its length. In this manner, the tapered strut is positionable between the engaging plates 12 and 14 to cause height 20 to decrease in a direction from anterior end 22 to posterior end 24 whereby the natural lordosis of the human spine is maintained by the fusion device. The degree of taper of the strut corresponds to a desired lordosis and may vary depending upon the size of the patient.

Figure 9:
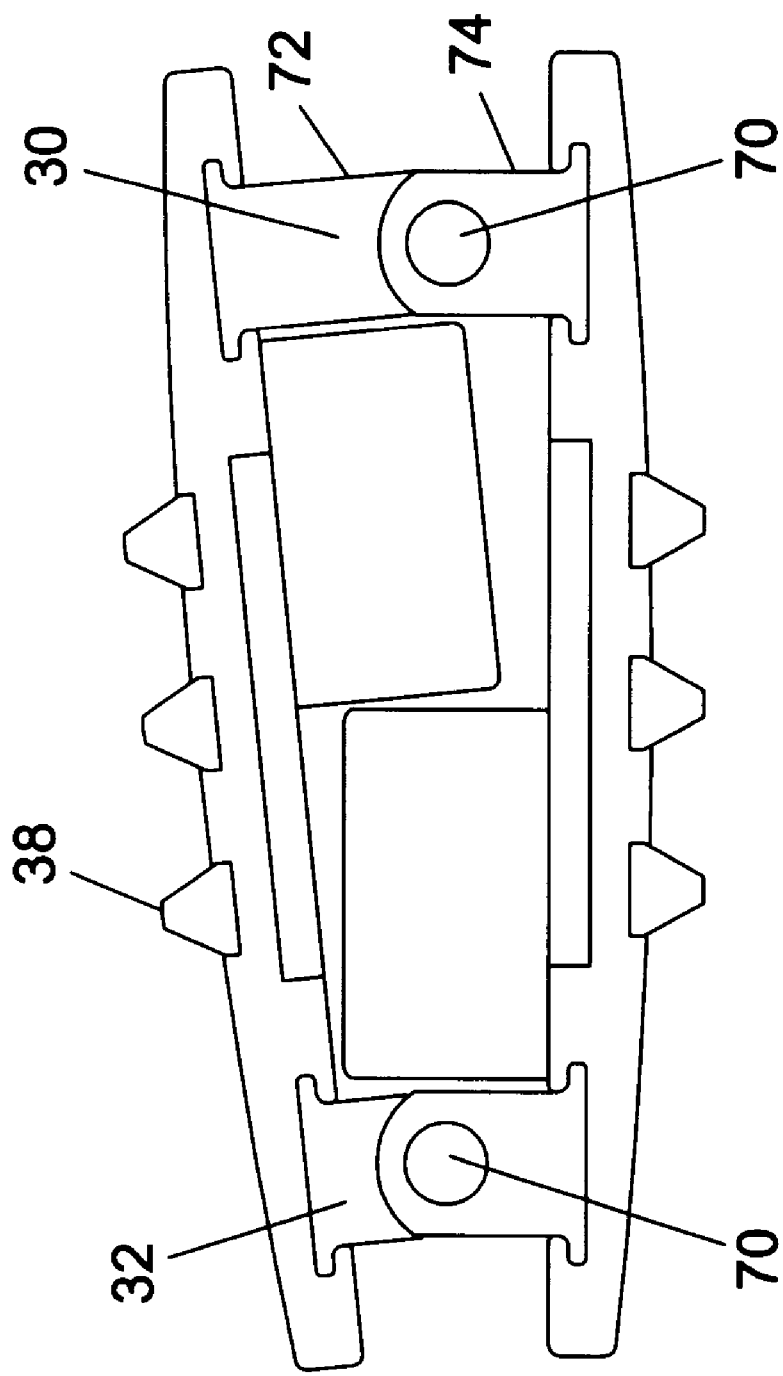
FIG. 9 depicts a front view of a fusion device having pivotable struts.

In an embodiment, the first and second struts have differing heights to cause height 20 to vary between first end 14 and second end 16. In this manner, the fusion device may be used to correct a lateral deviation in the spinal column as may occur in scoliosis. A front view of a fusion device containing struts having different heights is depicted in FIG. 9. Each of the struts preferably contains a hinge pin 70 to allow an upper member 72 of the strut to pivot with respect to a lower member 74 of the strut. In this manner, the struts may be pivoted as shown in FIG. 9 such that the ends of the struts are properly aligned with the slots of the engaging plates when a height difference exists between the first and second struts.

To install the fusion device, a discectomy is preferably performed from an anterior approach. All cartilage and soft tissue are preferably removed from the vertebral endplate as would normally be done for placement of a femoral strut graft. Such a procedure is well within the knowledge of a skilled practitioner of the art. The engaging plates may be deployed in the disc space between the adjacent vertebrae. A distraction force may be applied to the engaging plates using a laminae spreader or similar device to force the vertebrae to a selected height and lordotic alignment. The use of a laminae spreader is well known to those skilled in the art. The proper heights for the first and second struts may be determined beforehand using x-ray techniques in which the posterior and anterior portions of the intervertebral disc space are examined.

Appropriately sized and tapered struts are preferably slipped into slots 60 and tapped until a locking taper engagement is achieved between the strut ends and the slots. If struts of differing heights are used to correct for a lateral deviation in the spinal column, each strut may be pivoted about hinge pin 70 prior to insertion so that ends 50 are properly aligned for placement into grooves 60. Bone graft material is preferably inserted through the anterior end and packed between the engaging plates. Retaining plate 36 preferably prevents the bone graft material from passing through the fusion device during packing. Endcap 25 may then be placed onto the anterior end.

Figure 10:
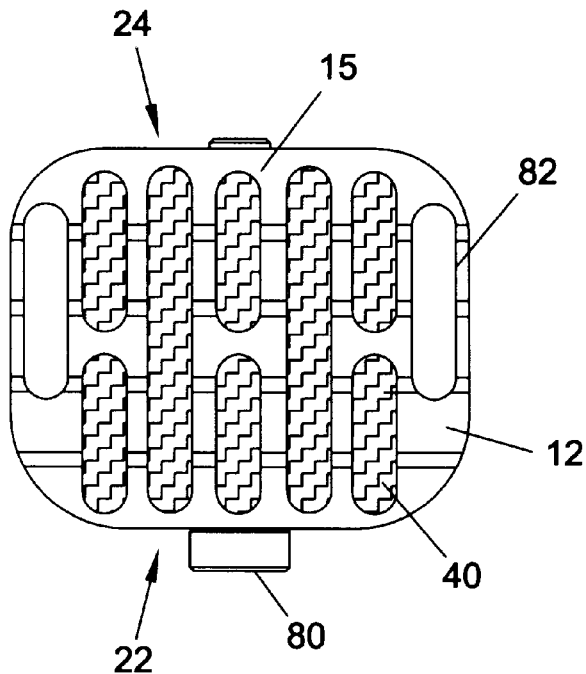
FIG. 10 depicts a top view of a fusion device containing a connector.

In an alternate embodiment depicted in FIGS. 10–16, the alignment device includes a connector 80 for adjusting the height 20 of the plates to achieve a desired lordotic alignment. FIG. 10 depicts a top view of the fusion device. Connector 80 is preferably a drive screw that is rotatable to adjust height 20. Connector 80 preferably extends between engaging plates 12 and 14 and may be adapted to move axially through the fusion device in a direction from anterior end 22 to posterior end 24. The engaging plates may contain elongated openings 82 for allowing bone growth through the faces 15 of the plates.

Figure 11:
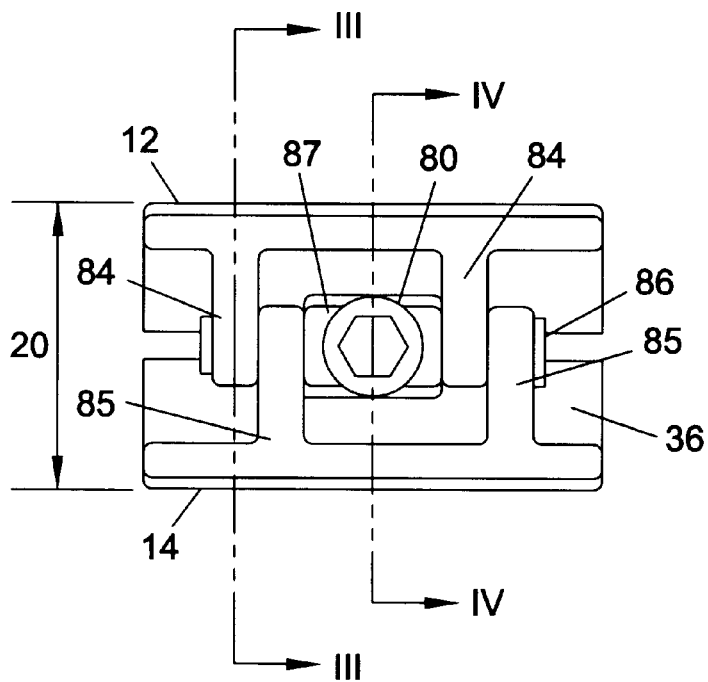
FIG. 11 depicts an anterior view of a fusion device having a connector and cam pins.
Figure 13:
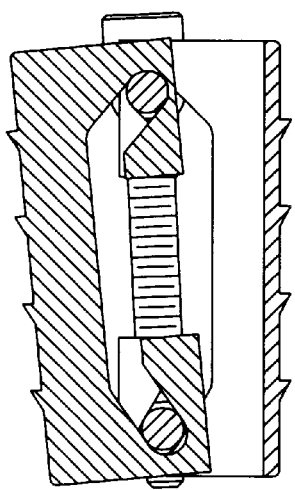
FIG. 13 depicts a cross-sectional view taken along plane III of FIG. 11 of the fusion device in a raised position.
Figure 12:
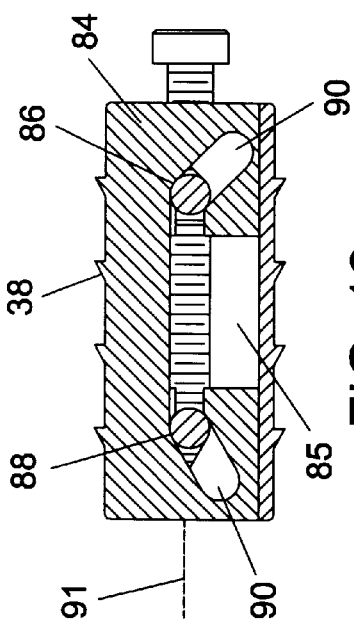
FIG. 12 depicts a cross-sectional view taken along plane III of FIG. 11 of the fusion device in a lowered position.

FIG. 11 depicts a front (anterior) view of the fusion device in a raised position. In an embodiment, the engaging plates include ribs 84 and 85 that may extend substantially perpendicularly from face 15. A cross-sectional view taken along plane III of FIG. 11 is depicted in each of FIG. 12 and FIG. 13. FIG. 12 depicts rib 84 and cam pins 86 and 88 in section with the fusion device in a "lowered position" (i.e., unadjusted for lordotic alignment). FIG. 13 depicts the rib and cam pins in section with the fusion device in the "raised position" (i.e., adjusted for lordotic alignment). As described herein, "cam pin" is taken to mean any connecting element capable of extending from the connector into the slots 90 and 92. Each of the cam pins may be intersected by an imaginary longitudinal axis 91 axially extending through the fusion device.

Rib 84 preferably contains a slot 90 having a first end and a second end. The ends of slot 90 preferably terminate in a direction below axis 91. The first end of slot 90 preferably extends downwardly substantially toward either the face of engaging plate 14 or the anterior end. The second end of slot 90 preferably extends downwardly substantially toward either the face of engaging plate 14 or the posterior end. Rib 85 preferably contains a slot 92 having a pair of ends that extend in diverging directions from the slot ends of rib 84. The ends of slot 92 preferably terminate in a direction above axis 91. The first end of slot 92 preferably extends upwardly substantially toward either the face of engaging plate 12 or the anterior end. The second end of slot 90 preferably extends upwardly substantially toward either the face of engaging plate 12 or the posterior end. The engaging plates are preferably connected together with cam pins 86 and 88, which preferably have ends sized to fit within slots 90 and 92. The cam pins preferably are disposed through the fusion device in a direction from the first side to the second side. Pins 86 and 88 preferably contain a receiving section 87 having an opening for receiving connector 80. Receiving section 87 may have a greater width (e.g., diameter) than the ends of pins 86 and 88 disposed in slots 90 and 92.

Figure 15:
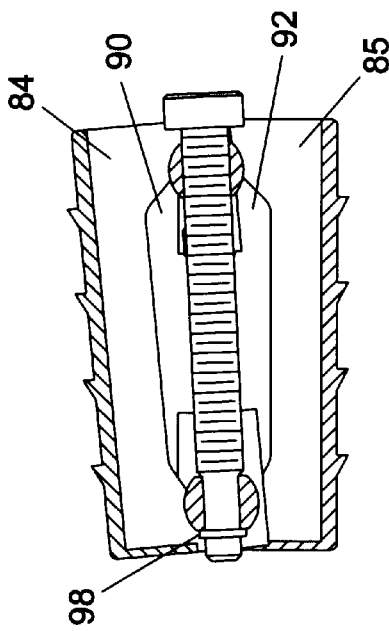
FIG. 15 depicts a cross-sectional view taken along plane IV of FIG. 11 of the fusion device in a raised position, the screw and retaining ring are not cross-sectioned in this figure.
Figure 14:
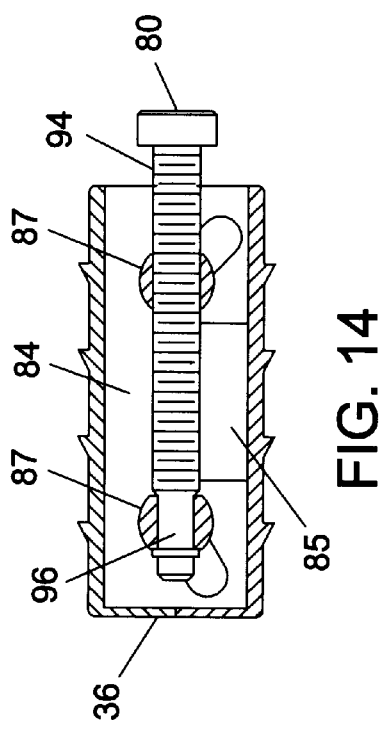
FIG. 14 depicts a cross-sectional view taken along plane IV of FIG. 11 of the fusion device in a lowered position, the screw and retaining ring are not cross-sectioned in this figure.

FIG. 14 and FIG. 15 each depict a cross-sectional view of the fusion device taken along plane IV of FIG. 11. FIG. 14 depicts the connector and cam pins in section with the fusion device in the lowered position. FIG. 15 depicts the connector and the cam pins in section with the fusion device in the raised position. In an embodiment, connector 80 contains a threaded portion 94 and an unthreaded portion 96. Pin 86 is preferably connected to the threaded portion and pin 88 is preferably connected to the unthreaded portion.

In an embodiment, a torque delivered to the connector is converted into a separation force between the cam pins. Rotating the connector in a counterclockwise direction preferably moves the connector in a direction from the anterior end to the posterior end. Pin 88 is preferably attached to the connector and preferably moves in the same manner as the connector. Pin 86 preferably contains an opening having complementary threading to that of the connector. Pin 86 preferably moves toward the anterior end in a direction opposite the motion of the connector to increase the separation between pin 88 and pin 86. The ends of the pins preferably move along the angled portions of the slots 90 and 92, causing the ends of the slots to be drawn together. In this manner, the separation between the engaging plates is increased. The connector may be rotated in a clockwise direction to move the connector in a direction from the posterior end to the anterior end, thereby decreasing height 20.

Conventional methods of surgically implanting fusion devices tend to require that distraction instruments, be inserted between the vertebrae to separate them and allow insertion of the fusion device therebetween. The surgical incision typically must be widened to accommodate the distraction instruments. In an embodiment, the fusion device in the lowered position has a height that is less than the disc space between the vertebrae. In this manner, the fusion device may be inserted between the vertebrae with minimal distraction. Connector 80 is preferably operable to separate the engaging plates (hence the vertebrae) and create a desired lordotic alignment.

The distance that the engaging plates are separated per unit torque applied to the connector will tend to depend upon the angle of the slots 90 and 92. The slots are preferably angled such that the height 20 proximate the anterior end changes at a greater rate than the height 20 proximate the posterior end when the connector is adjusted to alter the distance between the plates. In this manner, a desired lordotic alignment may be achieved. It is to be understood that the fusion device is operable in a semi-raised position that is intermediate the raised and lowered positions depicted in FIGS. 12–15. The connector is preferably rotated to a selected degree to achieve a preferred height 20 proximate the anterior and posterior ends to suit the particular patient. The angle of the slots 90 and 92 may vary among patients and is preferably selected to achieve a desired lordotic alignment. The connector may include a retaining ring 98 for contacting one or both of the engaging plates to limit the degree to which the connector can move through the fusion device.

Figure 16:
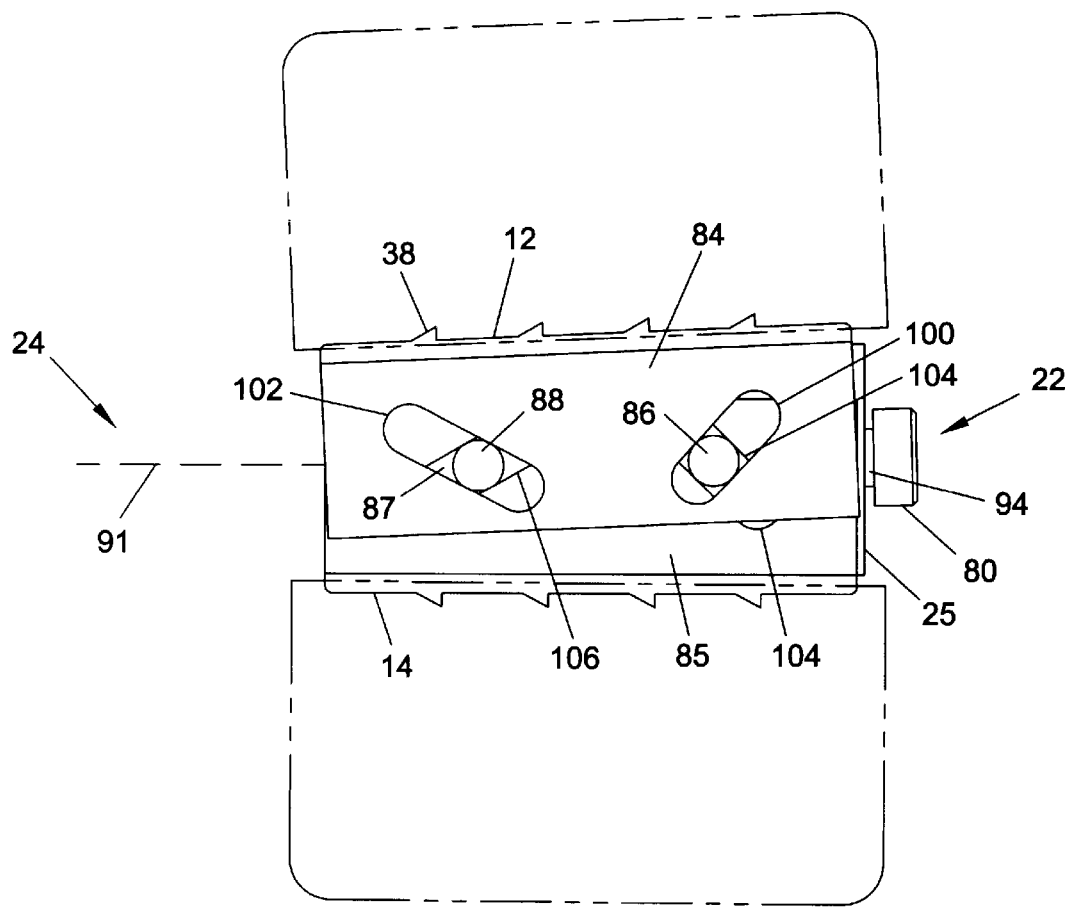
FIG. 16 depicts a side view of a fusion device disposed between vertebrae.

FIG. 16 depicts a side view of an alternate embodiment of the fusion device installed between neighboring vertebrae. Pin 86 may be located on the unthreaded portion of the shank adjacent to the head of connector 80. Pin 88 may be located on threaded portion 94 of the shank of connector 80. Rib 34 preferably includes a first slot 100 that is angled diagonally upward from axis 91 in a direction substantially toward either the face of engaging plate 12 or the anterior end 22. Rib 84 preferably also includes a second slot 102 that is angled diagonally upward from axis 91 in a direction substantially toward either the face of engaging plate 12 or the posterior end 24. Rib 85 preferably includes a first slot 104 that is angled diagonally downward from axis 91 in a direction substantially toward either the face of engaging plate 14 or the anterior end 22. Rib 85 preferably also includes a second slot 106 that is angled diagonally downward from axis 91 in a direction substantially toward either the face of engaging plate 14 or the posterior end 24. To adjust the fusion device into the raised position, the connector may be rotated to cause the cam pins to be moved in a direction toward one another. Pin 86 preferably moves with the connector in a direction from the anterior end to the posterior end to increase the separation between the engaging plates proximate the anterior end. Pin 88 preferably contains a threaded opening for receiving the connector and may move in a direction toward the posterior end to increase the separation between the engaging plates proximate the posterior end.

In an alternate embodiment, each of the pins 86 and 88 contains a threaded opening for receiving the connector 80. The connector may be a "double-threaded" screw having two threaded portions for complementing the threaded openings of the pins 86 and 88. Rotation of the screw in a first direction preferably causes the pins to move toward one another to increase the separation between the engaging plates. Rotation of the screw in an opposite direction preferably causes the pins to move away from one another to reduce the separation between the engaging plates.

In an alternate embodiment, the alignment device includes a load-sharing member to allow the engaging plates to move in response to a compressive force of predetermined magnitude. In accordance with Wolff's law, bone growth tends to occur in the presence of stress (e.g., load), and bone tends to be absorbed in the absence of stress. The load-sharing member preferably enables the fusion device to "share" compressive forces exerted onto the spinal column with the bone graft in the vicinity of the fusion device. The load-sharing member preferably is deflected upon receiving a predetermined force to cause the engaging plates to move, thereby shifting load from the fusion device to the bone graft proximate the fusion device. It is believed that providing a selected amount of stress to the bone graft in a such a manner will tend to result in a higher fusion rate as well as a stronger fusion mass.

Figure 18:
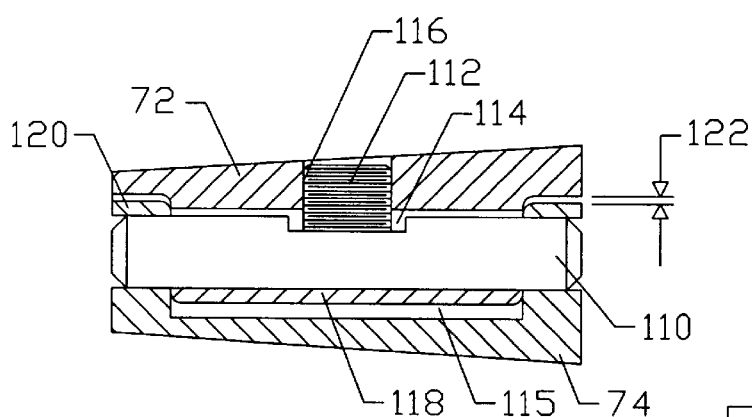
FIG. 18 depicts a cross-sectional view taken along plane V of FIG. 17 of the strut in an unloaded position.
Figure 19:
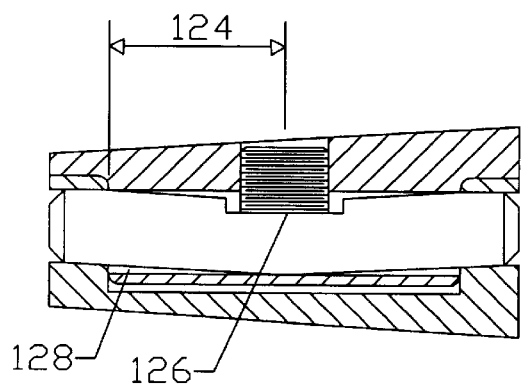
FIG. 19 depicts a cross-sectional view taken along plane V of FIG. 17 of the strut in a loaded position.

An embodiment of the load-sharing fusion device is depicted in FIGS. 17–19. A top view of a strut 30 containing a load-sharing member is depicted in FIG. 17. FIGS. 18 and 19 depict cross-sectional views of the strut taken along plane V of FIG. 17. Load-sharing member 110 is preferably disposed axially through the strut. The load-sharing member may be contained in a bore extending into the strut. The bore preferably has a width (e.g., diameter) that is greater than that of the load-sharing member to allow sufficient space for the load-sharing member to be deflected. The bore is preferably disposed within lower member 74. Portion 118 of the upper member may substantially surround the bore and the load-sharing member, thereby allowing attachment of the upper and lower members. In an embodiment, the load-sharing member is a pin having a substantially circular cross-section. The pin preferably fits loosely within the bore such that its rotational freedom is maintained. The pin may be hinge pin 70 about which the upper member 72 pivots with respect to the lower member 74. The load-sharing member preferably contains an indention 114 forming a substantially planar surface about which the load-sharing member may be deflected.

A connector 112 preferably extends through an opening 116 in the end 50 of the strut. The connector preferably fixes the load-sharing member to the upper member 72 and may contact the load-sharing member at fulcrum point 126, which is preferably located on the planar surface formed by indention 114. Connector 122 is preferably a set screw, and opening 116 preferably contains threading for engaging the set screw. FIG. 18 depicts the strut in an "unloaded" position whereby a predetermined spacing 122 exists between upper member 72 and portion 120 of lower member 74. The predetermined spacing 122 may be adjusted by altering the location of connector 112 within opening 116. For instance, the screw may be rotated through opening 116 lo increase spacing 122. The load-sharing member preferably remains substantially undeflected in the unloaded position.

Upon application of a compressive force onto the end 50 of the upper member 72, force is preferably imparted from connector 112 to the load-sharing member at fulcrum point 126. The compressive force is preferably sufficient to cause deflection of the load-sharing member and movement of upper member 72 toward portion 120 of the lower member such that predetermined spacing, 122 is decreased. The deflection of the load-sharing member may force portion 118 of the upper member into a cavity 1 15 formed within the axial bore. The load-sharing member is preferably deflected in a three point bending arrangement as shown in FIG. 19.

FIG. 19 depicts the strut in the "loaded" position with the load-sharing member deflected. The predetermined spacing 22 is preferably adjustable and may be adjusted to set the maximum strain that can be imparted to the load-sharing member. When the load-sharing member has been deflected a vertical distance equal to predetermined spacing 22, the upper member 72 contacts portion 120, thereby inhibiting further strain on the load-sharing member. In this manner, the maximum amount of strain on the load-sharing member can be limited to reduce the possibility that the member will experience fatigue failure.

The load-sharing member may be constructed of any of a variety of metals or alloys. In a preferred embodiment, the load-sharing member is constructed of titanium or a titanium alloy. The material properties and cross-sectional area of the load-sharing member are preferably controlled to allow a predetermined amount of stress to occur across the fusion device. The horizontal distance 124 or moment arm between fulcrum point 126 and support point 128 on the lower member is preferably selected such that the fusion device has an "effective" modulus of elasticity in the vicinity of the modulus of elasticity of bone to facilitate bone development. The "effective" modulus of elasticity of the fusion device is taken to mean the ratio of stress to strain across the fusion device in a direction along height 20 as the device moves from the unloaded position to the loaded position upon receiving a compressive force. As described herein, "in the vicinity of the modulus of elasticity of bone" is taken to mean a Young's modulus between about 3 GPa and about 25 GPa. In an embodiment, the effective modulus of the fusion device is between about 16 GPa and about 20 GPa. The paper entitled "Variation of Young's Modulus and Hardness in Human Lumbar Vertebrae Measured by Nanoindentation" by Marcel Roy and Jae-Young Rho (Department of Biomedical Engineering, University of Memphis, Memphis, Tenn.), and Ting Y. Tsui and George M. Pharr (Department of Materials Science, Rice University, Houston, Tex.) relates lo the mechanical properties of bone and is incorporated by reference as if fully set forth herein.

The stresses exerted onto the spinal column are preferably shared by the fusion device and surrounding bone graft. As the spinal fusion develops, the proportion of stress experienced by the surrounding bone material preferably increases and the required load on the fusion device preferably decreases. After completion of the fusion, the fusion device preferably remains in the unloaded position during normal daily activity of the patient.

Fusion device 10 preferably provides a relatively large contact area between the engaging plates and the vertebral bodies defining the disc space occupied by the fusion device. FIG. 20 depicts a top view of an embodiment of a fusion device of the present invention. FIG. 21 depict a cross-sectional view of the fusion device taken along plane VI of FIG. 20. Depicted in FIGS. 22–24 is a conventional fusion cage such as that described in U.S. Pat. No. 4,961,740 to Ray et al. This patent is incorporated by reference as if fully set forth herein. The devices in FIGS. 20–24 are sized for use in the L3–L4 disc space of an average size middle-aged female. Dimensions of the fusion devices are indicated in millimeters.

The "effective contact area" between an engaging plate and a vertebral body may be calculated by subtracting the fenestration area, a (i.e., the combined area of the openings 34 intended for bone ingrowth), from the total contact area, A (the area of the face 15 including the area of the openings 34). The total contact area and the fenestration area of the fusion device in FIGS. 20 and 21 is 581 mm$^2$ and 96 mm$^2$, respectively. Therefore, the effective contact area between the engaging plate and the vertebra is 485 mm$^2$.

For the fusion cage depicted in FIGS. 22–24, it is assumed that threads on the outer surface of the fusion cage penetrate into the vertebra a total of 3 mm per side as recommended by the manufacturer. It should be noted that such penetration is often difficult to achieve. In addition, the cortical layer of a vertebral body is often only 1–2 mm thick. Each of the cylindrical elements of the fusion cage has a total contact area of 283.5 mm$^2$ and a fenestration area of 198.5 mm$^2$. Therefore, the combined effective contact area of both of the cylindrical elements is 170 mm$^2$. If the threads of the fusion cage penetrate into the vertebra a distance less than 3 mm per side, the contact area will be less than that calculated above.

The maximum axial compressive forces in the lumbar spine resulting from everyday activity were estimated to be 3200 N in a paper entitled "The BAK™ Interbody Fusion: An Innovative Solution" by Bagby et al. and available from Spine Tech, Inc. in Minneapolis Minn. (see page 3, bottom paragraph). For a 3200 N compressive force, the stress per unit area is calculated to be 18.8 N/mm² for the fusion cage depicted in FIGS. 22–24 as compared to 6.6 N/mm² for the fusion device depicted in FIG. 20 and FIG. 21. It is believed that such a reduction in stress per unit area will result in a significant reduction in post surgical subsidence at the interface of the fusion device and vertebral body. Typically, the loss of disc height is estimated to be about 1–3 mm at one month follow-up when conventional devices such as that depicted in FIGS. 22–24 are employed.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A spinal implant for facilitating a fusion between neighboring vertebrae of a human spine, comprising:
   a first side opposite a second side;
   a pair of engaging plates adapted to fit between and engage the vertebrae to maintain a disk space between the vertebrae during use;
   a plurality of slots in each engaging plate, wherein each slot has at least one slanted section;
   a first pin and a second pin, wherein a portion of the first pin and a portion of the second pin are adapted to be positioned between the engaging plates on the slanted sections of the plurality of slot, the pins being substantially elongated and positioned to extend in a direction from the first side to the second side during use; and
   a connector for engaging the pins, wherein rotation of the connector causes movement of the first pin and the second pin along slanted sections of the slots to alter a separation distance between the engaging plates during use.

2. The spinal implant of claim 1 wherein the engaging plates are substantially planar so as to inhibit subsidence of the vertebrae.

3. The spinal implant of claim 1 wherein the engaging plates comprise a plurality of openings to allow bone growth to occur through the engaging plates.

4. The spinal implant of claim 1 wherein the engaging plates comprise a plurality of openings, and further comprising bone graft packed between the engaging plates.

5. The spinal implant of claim 1, further comprising protrusions extending from at least one of the engaging plates for enhancing an engagement between the vertebra and the engaging plate.

6. The spinal implant of claim 1, further comprising a retaining plate proximate the posterior end for maintaining bone graft between the engaging plates.

7. The spinal implant of claim 1, further comprising a removable end cap proximate the anterior end for maintaining bone graft between the engaging plates.

8. The spinal implant of claim 1 wherein at least one of the engaging plates comprises a face and openings, the openings extending through the face to allow bone growth to occur through the engaging plate, and wherein the openings have a total area that is between about 60 percent and about 80 percent of a total surface area of the face.

9. The spinal implant of claim 1 wherein at least one of the engaging plates comprises a face and openings, the openings extending through the face to allow bone growth to occur through the engaging plate, and wherein the openings have a total area that is greater than about 50 percent of a total surface area of the face.

10. The spinal implant of claim 1 wherein the connector is a screw having a threaded portion, said threaded portion configured to engage a threaded portion of the first pin.

11. The spinal implant of claim 1 wherein the engaging plates comprise titanium.

12. The spinal implant of claim 1 wherein the engaging plates each further comprise a rib and a face, the rib extending in a substantially perpendicular direction from the face, the rib comprising the slot for receiving one of the pins.

13. The spinal implant of claim 1 wherein the engaging plates each further comprise a rib comprising the slot into which the pins extend.

14. The spinal implant of claim 1 wherein the connector is a screw adapted to move axially between the engaging plates, and wherein the screw further comprises a retaining ring for contacting a portion of at least one of the engaging plates to limit movement of the screw.

15. The spinal implant of claim 1 wherein the first pin comprises a threaded opening, and wherein the connector is a screw comprising a threaded portion and an unthreaded portion, the threaded portion extending through the threaded opening, the second pin being connected to the unthreaded portion.

16. The spinal implant of claim 1, further comprising an anterior end and a posterior end, and wherein the connector is adapted to move axially between the engaging plates in a direction from the anterior end to the posterior end, thereby moving the first pin toward the anterior end and the second pin toward the posterior end to increase the height.

17. The spinal implant of claim 1 wherein one of the slots comprises a first end and wherein the other slot comprises a second end, the first end and the second end extending in diverging directions, and wherein movement of one of the pins draws the first end and the second end together.

18. The spinal implant of claim 1 wherein the pins comprise an end and a receiving section, the end being disposed within one of the slots, the receiving section containing an opening for receiving the connector, the receiving section having a greater width than the end of the pin.

19. The spinal implant of claim 1 wherein the engaging plates each further comprise a rib and a face, the rib extending from the face in substantially perpendicular direction, and wherein the slot extends along a length of the rib.

20. The spinal implant of claim 1, further comprising an anterior end and a posterior end, and wherein movement of the pins alters the height proximate the anterior end at a faster rate than the height proximate the posterior end.

21. A spinal implant for facilitating a fusion between neighboring vertebrae of a human spine, comprising:
   a pair of engaging plates adapted to fit between and engage the vertebrae to maintain a disk space between the vertebrae during use;
   a plurality of ribs connected to each engaging plate, wherein the ribs provide a space and a separation distance between faces of the engaging plates;

a plurality of slots in the ribs, each slot having at least one slanted section, a first pin positionable on slanted sections of the plurality of slots, the first pin configured to couple the pair of engaging plates together;

a second pin positionable on slanted sections of the plurality of slots, the second pin configured to couple the pair of engaging plates together; and a connector coupled to the first pin and the second pin;

wherein rotation of the connector causes movement of the pins along the slanted sections of the slots to alter the separation distance between the engaging plates during use.

22. The spinal implant as defined in claim 21, wherein the faces of the engaging plates are configured to contact the vertebrae, and wherein the faces are substantially planar so as to inhibit subsidence of the vertebrae during use.

23. The spinal implant as defined in claim 21, further comprising at least one protrusion extending from at least one of the engaging plates for enhancing engagement between the vertebrae and the engaging plates during use.

24. The spinal implant as defined in claim 21, wherein the connector is a screw having a threaded portion configured to engage threading on the first pin.

25. The spinal implant as defined in claims 24, further comprising a retaining ring between an end of the screw and edges of the pair of engaging plates to inhibit movement of the end of the screw between the engaging plates.

26. The spinal implant as defined in claim 21, wherein at least one of the engaging plates further comprises openings, said openings extend through the face.

27. The spinal implant as defined in claim 26 wherein the openings have a total area that is greater than about 50 percent of a total surface area of the face.

28. The spinal implant as defined in claim 26, wherein the openings have a total area that is between about 60 percent and about 80 percent of a total surface area of the face.

29. The spinal implant as defined in claim 26, further comprising bone graft packed between the engaging plates.

* * * * *

UNITED STATES PATENT AND TRADEMARK OFFICE
CERTIFICATE OF CORRECTION

PATENT NO.   : 6,080,193
DATED        : June 27, 2000
INVENTOR(S)  : Hochschuler et al.

It is certified that error appears in the above-identified patent and that said Letters Patent is hereby corrected as shown below:

<u>Title page,</u>
Item [19], in the inventor identification, please delete "Hochshuler et al." and insert
-- Hochschuler et al. --.
Item [75], in the Inventor field, please delete "Stephen H. Hochshuler" and insert
-- Stephen H. Hochschuler --.

Signed and Sealed this

Thirteenth Day of August, 2002

*Attest:*

JAMES E. ROGAN
*Attesting Officer*   *Director of the United States Patent and Trademark Office*